(12) United States Patent
Ried et al.

(10) Patent No.: US 6,294,331 B1
(45) Date of Patent: *Sep. 25, 2001

(54) METHODS FOR ASSESSING GENETIC AND PHENOTYPIC MARKERS BY SIMULTANEOUS MULTICOLOR VISUALIZATION OF CHROMOGENIC DYES USING BRIGHTFIELD MICROSCOPY AND SPECTRAL IMAGING (75) Inventors: Thomas Ried, Bethesda, MD (US); Merryn V. E. MacVille, The Hague; Anton H. N. Hopman, Eijsden, both of (NL)

(73) Assignee: The United States of America as represented by the Department of Health and Human Services, Washington, DC (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/130,078

(22) Filed: Aug. 7, 1998

Related U.S. Application Data (60) Provisional application No. 60/055,439, filed on Aug. 8, 1997.

(51) Int. Cl.⁷ .............................. C12Q 1/68; C12N 15/11; G02B 21/12
(52) U.S. Cl. .............................. 435/6; 435/7.1; 435/7.92; 536/24.3; 359/368
(58) Field of Search ................................ 435/6, 7.1, 7.92; 536/24.3; 359/368

(56) References Cited

FOREIGN PATENT DOCUMENTS

WO 97/21979    6/1997 (WO) .
WO 97/22848    6/1997 (WO) .

OTHER PUBLICATIONS

Malik et al. Fourier transform multipixel spectroscopy for quantitative cytology. J. Microscopy vol. 182 pp. 133–140, 1995.*
Schröck, et al., "Multicolor Spectral Karyotyping of Human Chromosomes", *Science*, vol. 273, pp. 494–497, Jul., 1996.
Speel, et al., "Cytochemical detection systems for in situ hybridization, and the combination with immunocytochemistry. 'Who is still afraid of Red, Green and blue?'", *Histochemical Journal*, 27:833–858, 1995.
Garini, et al., "Spectral karyotyping", *Bioimaging*, 4:65–72, 1996.

* cited by examiner

*Primary Examiner*—John S. Brusca
(74) *Attorney, Agent, or Firm*—Needle & Rosenberg (57) ABSTRACT

The present invention is directed to an improved method for detecting a genetic marker in a biological sample comprising contacting the biological sample with a nucleic acid probe linked to a detectable moiety, whereby the detectable moiety can be detected by the presence of a chromogenic dye associated with the detectable moiety, obtaining a spectral image of the biological sample using brightfield microscopy, and detecting the presence of the chromogenic dye, thereby detecting the genetic marker in the biological sample. The present invention also provides an improved method for detecting a phenotypic marker in a biological sample comprising contacting the biological sample with a compound comprising a detectable moiety, whereby the compound associates with the phenotypic marker and whereby the detectable moiety can be detected by the presence of a chromogenic dye associated with the detectable moiety, obtaining a spectral image of the biological sample using brightfield microscopy, and detecting the presence of the chromogenic dye, thereby detecting the phenotypic marker in the biological sample.

7 Claims, 3 Drawing Sheets

(3 of 3 Drawing Sheet(s) Filed in Color)

Absorption spectra raw spectral image optical density classification

FIG. 1

New Fuchsin with heavy Hematoxilin staining

Absorption spectra raw spectral image     optical density     classification

METHODS FOR ASSESSING GENETIC AND PHENOTYPIC MARKERS BY SIMULTANEOUS MULTICOLOR VISUALIZATION OF CHROMOGENIC DYES USING BRIGHTFIELD MICROSCOPY AND SPECTRAL IMAGING

This application claims the benefit of U.S. Provisional Application No. 60/055,439, filed Aug. 8, 1997.

BACKGROUND OF THE INVENTION

1. Field of the Invention

This invention relates to methods of detecting genetic and phenotypic markers in biological samples using spectral imaging and brightfield microscopy to detect the presence of chromogenic dyes.

2. Background Art

In cytopathological diagnostic laboratories, cytological specimens are routinely stained with permanent dyes such as hematoxylin and eosin and for decades, pathologists have based their diagnosis of disease on cyto- and histological features as seen under a light microscope. Unlike fluorescent dyes, permanent dyes do not fade or bleach so that second opinion diagnosis, re-examination of archived material and even retrospective studies, can be performed. Thus, for routine cytopathological diagnostic purposes, fluorescence microscopy is not preferred for these reasons as well as because of high auto-fluorescence inherent to the tissue type or which might be induced by fixation.

Immunohistochemical and in situ hybridization methods have become increasingly important for research and diagnosis of disease. Also, multi-parameter cytochemical analysis is required when rare or unique material is to be studied. Many fluorescent markers with emission spectra ranging from blue to infra-red have become available for multi-color detection due to advances made in conjugation chemistry. Thus, although fluorescence microscopy could be used for these multi-parameter applications, for the above-mentioned reasons, it is often not possible to use methods employing fluorescence.

The present invention overcomes previous shortcomings in the art by providing methods for analyzing both genetic and phenotypic markers in a single biological sample through the use of bright field spectral imaging of chromogenic dyes. Such analyses are valuable in a variety of clinical applications, such as, for example, the diagnosis and characterization of cancer and the analysis of chromosomal aberrations in pre- and post-natal diagnostics.

An important aspect of the present invention that overcomes a severe limitation in the art is that by using the methods provided herein, multiple probes, both to genetic and/or phenotypic markers, and therefore multiple chromogenic dyes can be used in the same sample and the individual dyes can be distinguished using spectral imaging, even where the sample has been previously stained with a cytological stain which otherwise would obscure the signal from the genetic or phenotypic probes. Using these methods, a pathologist for example, can stain a tissue sample to observe a general morphological aspect of cells in the sample, and a geneticist can subsequently use that stained sample to diagnose cells in the sample for the presence of a genetic or phenotypic marker, such as a chromosomal aberration associated with cervical cancer, with much more clarity, accuracy, ease, and efficiency than using previously available methods.

SUMMARY OF THE INVENTION

In accordance with the purpose(s) of this invention, as embodied and broadly described herein, this invention, in one aspect, relates to the present invention provides an improved method for detecting a genetic marker in a biological sample comprising contacting the biological sample with a nucleic acid probe linked to a detectable moiety, whereby the detectable moiety can be detected by the presence of a chromogenic dye associated with the detectable moiety, obtaining a spectral image of the biological sample using brightfield microscopy, and detecting the presence of the chromogenic dye, thereby detecting the genetic marker in the biological sample.

The present invention also provides an improved method for detecting a phenotypic marker in a biological sample comprising contacting the biological sample with a compound comprising a detectable moiety, whereby the compound associates with the phenotypic marker and whereby the detectable moiety can be detected by the presence of a chromogenic dye associated with the detectable moiety, obtaining a spectral image of the biological sample using brightfield microscopy, and detecting the presence of the chromogenic dye, thereby detecting the phenotypic marker in the biological sample.

Additional advantages of the invention will be set forth in part in the description which follows, and in part will be obvious from the description, or may be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

The accompanying figures, which are incorporated in and constitute a part of this specification, illustrate several embodiments of the invention and together with the description, serve to explain the principles of the invention.

BRIEF DESCRIPTION OF THE DRAWINGS

The file of this patent contains at least one drawing executed in color. Copies of this patent with color drawings will be provided by the Patent and Trademark Office upon request and payment of the necessary fee.

FIG. 1. Triple color spectral imaging of T24 cells, using chromosome 1, 7 and 15 centromere-specific probes. Targets were visualized with, respectively, DAB, NF and TMB. Bottom left shows the raw spectral image of the hybridization signals of one cell. The colors are a result of an arbitrary RGB look-up table and do not display the colors as seen through the microscope. Bottom center shows the spectral image after calculation of absorption spectra. Constituents that absorb light are displayed in the complementary color. As a consequence, areas that don't absorb appear black. Top shows spectra of three pixels located on the different dyes in an absorption intensity per wavelength diagram. The absorption peaks are wide apart and the shape of the curves differ significantly. Bottom right shows the result of a spectrum based classification whereby pixels with similar spectral information are assigned the same false color. This classification is based on the input of the spectra shown in the diagram. The DAB spots (4) are false-colored with a brown color, TMB (2) with green and NF (3) with red. The spectrum of the unstained nucleus differed sufficiently from the background light to be classified in a blue color.

FIG. 2. T24 cells hybridized for centromere of chromosome 7 and visualized with NF. The nucleus is stained with hematoxylin. Bottom left shows the raw spectral image in arbitrary colors. Bottom center shows the spectral image after calculation of the absorption spectra displayed in complementary colors. Top shows the spectra of a few pixels over the spots and the nucleus. The spectra of the spots is the sum of the spectra for NF and hematoxylin (compare with NF spectrum in FIG. 1 bottom left), whereas the spectrum of the nucleus is solely hematoxylin. Based on the average spectra of the selected pixels, a classification is performed, shown bottom right. Spots and nuclei are false-colored in red and blue, respectively.

DETAILED DESCRIPTION OF THE INVENTION

The present invention may be understood more readily by reference to the following detailed description of preferred embodiments of the invention and the Example included therein and to the Figures and their previous and following description.

Before the present compounds, compositions and methods are disclosed and described, it is to be understood that this invention is not limited to specific methods, specific nucleic acid probes, cytological stains, detectable moities, etc., as such may, of course, vary. It is also to be understood that the terminology used herein is for the purpose of describing particular embodiments only and is not intended to be limiting.

It must be noted that, as used in the specification and the appended claims, the singular forms "a," "an" and "the" include plural referents unless the context clearly dictates otherwise. Thus, for example, reference to "a nucleic acid probe" includes multiple nucleic acid probe molecules.

The present invention provides methods by which the assessment of histological or cytological preparations can be combined with detection of genetic and phenotypic markers by using spectral imaging.

From a technical point of view, in multi-target labeling format, color discrimination by eye through a bright field light microscope is difficult, if not impossible in common situations where: 1) the staining is weak; 2) signals are small (e.g. they appear as small punctuate dots); 3) signals lay close together or merge; or 4) signals overlap in z-direction.

In addition, cytological stains can obscure the color information from the signals.

Color discrimination based on 3-color CCD video images can be performed by measuring the hue value. Hue values are introduced to specify colors numerically. Calculation is based on intensities of red, green and blue light (RGB) as recorded by the separate channels of the camera. The formulation used for transforming the RGB values into hue, however, simplifies the data and does not make reference to the true physical properties of light. In contrast, spectral imaging analyzes light as the intensity per wavelength, which is the only quantity by which to describe the color of light correctly. In addition, spectral imaging provides spatial data, because it contains spectral information for every pixel in the image.

Thus, the present invention provides an improved method for detecting a genetic marker in a biological sample comprising contacting the biological sample with a nucleic acid probe linked to a detectable moiety, whereby the detectable moiety can be detected by the presence of a chromogenic dye associated with the detectable moiety, obtaining a spectral image of the biological sample using brightfield microscopy, and detecting the presence of the chromogenic dye, thereby detecting the genetic marker in the biological sample.

The present invention also provides an improved method for detecting a phenotypic marker in a biological sample comprising contacting the biological sample with a compound comprising a detectable moiety, whereby the compound associates with the phenotypic marker and whereby the detectable moiety can be detected by the presence of a chromogenic dye associated with the detectable moiety, obtaining a spectral image of the biological sample using brightfield microscopy, and detecting the presence of the chromogenic dye, thereby detecting the phenotypic marker in the biological sample.

The method of detecting genetic and phenotypic markers in a biological sample can be used for diagnosing cancer, identifying types of cancer; determining a prognosis of a cancer, as well as for detecting, identifying, diagnosing, characterizing and/or determining a prognosis of a variety of other disease states or abnormal conditions which can be detected, identified, characterized, etc., by genetic and/or phenotypic markers in a biological sample. The method of the present invention can also be applied to pre- and postnatal diagnostics. For each of these methods, the biological sample can be prepared as described herein or by various other methods which are well known in the art for preparing biological samples for genetic and phenotypic analyses.

It is further contemplated that the present invention provides methods for detecting genetic and phenotypic markers in a biological sample for comparative cytogenetics (i.e., interspecies studies) and karyotyping. For these methods, the biological sample can be prepared according the methods described herein or according to various methods well known in the art for preparing biological samples for genetic and phenotypic analysis relating to comparative cytogenetics and karyotyping.

Detection of phenotypic and genetic markers in a biological sample can be by microscopy, which can be, but is not limited to, bright-field microscopy, phase contrast microscopy, interference contrast microscopy, Nomarski contrast microscopy, dark field microscopy, reflection contrast microscopy, fluorescence microscopy, infra-red microscopy, or any other type of light microscopy. Detection can be done by visualizing the biological sample in the microscope or by recording an image of the biological sample photographically (e.g., by producing an image on a silver halide emulsion film which can be developed for visualization or by recording a digital image of the sample for visualization via an output device, such as, for example, a computer monitor or as a computer printout) as well as by any other means by which the biological sample can be viewed or recorded. The spectral image of the biological sample can be taken from the sample directly or from a recorded image of the sample.

The biological sample of this invention can be from any organism and can be, but is not limited to, embedded tissue sections, frozen tissue sections, cell preparations, cytological preparations, exfoliate samples (e.g., sputum), fine needle aspirations, amnion cells, fresh tissue, dry tissue, and cultured cells or tissue. It is further contemplated that the biological sample of this invention can also be whole cells or cell organelles (e.g., nuclei). The biological sample can be unfixed or fixed according to standard protocols widely available in the art and can also be embedded in a suitable medium for preparation of the sample. For example, the biological sample can be embedded in paraffin or other suitable medium (e.g., epoxy or acrylamide) to facilitate preparation of the biological specimen for the detection methods of this invention. Furthermore, the biological sample can be embedded in any commercially available mounting medium, either aqueous or organic, depending on the chemical properties of the stain or any specifically developed medium, such as, for example, as designed for TMB, based on a thin protein layer cross-linked by formaldehyde to ensure permanent stabilization of the enzyme reaction products (Speel et al., 1994. A novel triple-color detection procedure for brightfield microscopy, combining in situ hybridization with immunocytochemistry." *J. Histochem. Cytochem.* 42:1299–1307).

The biological sample can be on, supported by, or attached to, a substrate which facilitates detection of phenotypic or genetic markers. A substrate of the present invention can be, but is not limited to, a microscope slide, a culture dish, a culture flask, a culture plate, a culture chamber, DNA arrays, ELISA plates, as well as any other substrate now known or developed in the future for containing or supporting biological samples for analysis according to the methods of the present invention. The substrate can be of any material suitable for the purposes of this invention, such as, for example, glass, plastic, polystyrene, mica and the like. The substrates of the present invention can be obtained from commercial sources or prepared according to standard procedures well known in the art.

The detection of phenotypic and genetic markers in the biological sample can be combined with the routine assessment of histological and cytological specimens, generally carried out by staining with one or more cytological stains and examining the specimens microscopically. Thus, the present invention provides for multi-parameter analyses of the same biological sample.

The biological sample of the present invention can be contacted with one or more cytological stains. The cytological stains used in the methods of this invention can be, but are not limited to, hematoxylin, eosin, methyl green, neutral red, DIFF QUIK (Baxter, The Netherlands), toluidine blue, alcian blue, isamin blue, methylene blue, sudan black, periodic acid-Schiff reaction (PAS), Masson's trichrome method, reticulin stain, Van Gieson, Azan, Giemsa, NissI, silver and gold stains, osmium and chrom alum, as well as any other cytological stains now known or identified in the future. The cytological stains of this invention are available from commercial sources or can be prepared according to standard methods well known in the art.

The phenotypic markers identified by the methods of this invention can be, but are not limited to, messenger RNA, gene products, antigens, antibodies, and proteins, or fragments thereof, which can be of, for example, tumor suppressor genes, oncogenes and proliferation markers. Examples of gene products which can be detected as phenotypic markers can include, but are not limited to, gene products of p53, retinoblastoma, Ki67, PCNA, nucleolus organizing regions and cyclins. These phenotypic markers can be detected by methods well known in the art, including modifications of the methods described herein to detect nucleic acid probes, such as binding to the phenotypic marker a detectable molecule such as a nucleic acid, a hapten, a protein, an antigen, and an antibody, or fragments thereof.

The compound or compounds comprising a detectable marker which are used to detect a phenotypic marker, therefore, include any compound which can bind to, link to, hybridize to, or otherwise associate with the phenotypic marker. For example, the compound can be an antibody to a protein or a fragment of a protein, an antibody to a nucleic acid, an antibody to a ligand or a fragment of a ligand, an antibody to an antibody or fragment of an antibody (anti-idiotype antibody), an antibody to any cellular structure or fragment of the cellular structure, and the like. Alternatively, the compound can comprise other molecules such as nucleic acids, ligands, haptens, cell structures, and fragments thereof.

The genetic markers of this invention can be, but are not limited to, centromeres, telomeres, general or specific loci, chromosome bands, a chromosome-specific loci, chromosome fragments, and whole chromosomes, as well as any genetic marker which detects numerical chromosome alterations or structural chromosome alterations such as translocations, breakpoints, microdeletions and amplifications. For detection of these genetic markers, a nucleic acid probe having complementarity to the nucleotide sequence of the genetic marker is contacted with the biological sample under conditions whereby hybridization of the nucleic acid of the genetic marker and the nucleic acid probe can occur. These conditions can vary, depending of the biological sample, genetic marker and nucleic acid probe used for a given application. The hybridization conditions for a particular application can be determined according to protocols standard in the art. Examples of various hybridization conditions are provided in the Examples herein.

The nucleic acid probe of this invention can be a nucleic acid comprising the nucleotide sequence of a coding strand or its complementary strand or the nucleotide sequence of a sense strand or antisense strand. Thus, the probe of this invention can be either DNA or RNA and can bind either DNA or RNA, or both, in the biological sample. The probe can be the coding or complementary strand of a complete gene or gene fragment. The nucleotide sequence of the probe can be any sequence having sufficient complementarity to a nucleic acid sequence in the biological sample to allow for hybridization of the probe to the target nucleic acid in the biological sample under a desired hybridization condition. Ideally, the probe will hybridize only to the nucleic acid target of interest in the sample and will not bind non-specifically to other non-complementary nucleic acids in the sample or other regions of the target nucleic acid in the sample. The hybridization conditions can be varied according to the degree of stringency desired in the in situ hybridization. For example, if the hybridization conditions are for high stringency, the probe will bind only to the nucleic acid sequences in the sample with which it has a very high degree of complementarity. Low stringency hybridization conditions will allow for hybridization of the probe to nucleic acid sequences in the sample which have some complementarity but which are not as highly complementary to the probe sequence as would be required for hybridization to occur at high stringency. The hybridization conditions will vary depending on the biological sample, probe type and target. An artisan will know how to optimize hybridization conditions for a particular application of the present method. Examples of hybridization conditions are described in the Examples provided herein.

The nucleic acid probe can be commercially obtained or can be synthesized according to standard nucleotide synthesizing protocols well known in the art. Alternatively, the probe can be produced by isolation and purification of a nucleic acid sequence from biological materials according to methods standard in the art of molecular biology (Sambrook et al. 1989. *Molecular Cloning: A Laboratory Manual*, 2d Ed., Cold Spring Harbor Laboratory Pres, Cold Spring Harbor, N.Y.). The nucleic acid probe can be amplified according to well known procedure for amplification of nucleic acid (e.g., polymerase chain reaction). Furthermore, the probe of this invention can be linked to any of the detectable moieties of this invention by protocols standard in the art.

It is further contemplated that the present invention also includes methods for oligonucleotide hybridization wherein the hybridized oligonucleotide is used as a primer for an enzyme catalyzed elongation reaction such as in situ PCR and primed in situ labeling reactions whereby haptenized nucleotides are incorporated in situ. Additionally included are methods for in situ hybridization, employing synthetic peptide nucleic acid (PNA) oligonucleotide probes (Nielsen et al., 1991. "Sequence-selective recognition of DNA by strand displacement with a thymine-substituted polyamide." *Science* 254:1497–1500; Egholm et al., 1993. "PNA hybridizes to complementary oligonucleotides obeying the Watson-Crick hydrogen bonding rules." *Nature* 365:566–568).

The detectable moieties to which the nucleic acid probe of this invention can be linked to include, but are not limited to, a hapten, biotin, digoxigenin, fluorescein isothiocyanate (FITC), dinitrophenyl, amino methyl coumarin acetic acid, acetylaminofluorene and mercury-sulfhydryl-ligand complexes, as well as any other molecule or compound which can be linked to a nucleic acid probe and detected either directly or indirectly according to the methods described herein.

In one method of detection, the nucleic acid or compound moiety can be directly detected by linking the detectable moiety to the nucleic acid probe or compound and another moiety which can facilitate direct detection, such as an enzyme (e.g., peroxidase, alkaline phosphatase, glucose oxidase) which produces a colored reaction product when reacted with a suitable substrate or to colloidal gold particles or other detectable moieties. Alternatively, the nucleic acid or compound can be detected indirectly by the binding of antibodies, antibody fragments or other ligands, or the reaction of other molecules (e.g., avidin to detect biotin) with the detectably moiety linked to the nucleic acid or compound, including for example, enzymes such as peroxidase, alkaline phosphatase or glucose oxidase for enzymatic precipitation upon reaction with suitable substrates to produce a colored reaction product, i.e., a chromogenic dye associated with the detectable moiety. The enzyme peroxidase can also be used in conjunction with tyramide-based detection formats.

The antibodies, antibody fragments or ligands can also be linked to colloidal gold particles for direct detection or subsequently enhanced with silver for indirect detection. The detectable moieties of this invention are available from commercial sources or can be prepared according to standard protocols well known in the art. Methods for detecting the detectable moieties of the present invention are common in the art. Protocols for linking probes, detectable moieties, antibodies, ligands, etc., are also standard in the art and are readily available to the artisan. Additionally, the detectable moieties exemplified here can be detected in any number of alternative detection procedures other than those listed.

The detectable moiety of this invention can also comprise an antibody. The antibody can be either monoclonal or polyclonal. The antibodies of this invention can also include immunoreactive antibody fragments. The detectable moiety can also comprise a ligand or any other molecule that can detect the antibody or the nucleic acid probe.

Antibodies can be made by many well-known methods (See, e.g. Harlow and Lane, "*Antibodies; A Laboratory Manual*" Cold Spring Harbor Laboratory, Cold Spring Harbor, N.Y., (1988)). Briefly, purified antigen can be injected into an animal, with or without adjuvants, in an amount and in intervals sufficient to elicit an immune response. Polyclonal antibodies can be purified directly, or spleen cells can be obtained from the animal for monoclonal antibody production. The spleen cells can be fused with an immortal cell line and the resulting hybridomas can be screened for antibody secretion. A variety of immunoassay formats can be used to select antibodies which selectively bind with a particular protein. For example, solid-phase ELISA immunoassays are routinely used to select antibodies selectively immunoreactive with a protein. See Harlow and Lane (1988) for a description of immunoassay formats and conditions that can be used to characterize antibody binding.

In some instances, it is desirable to prepare monoclonal antibodies from various hosts, for example, for anti-species antibodies. A description of techniques for preparing such monoclonal antibodies may be found in Stites et al., editors, "Basic and Clinical Immunology," (Lange Medical Publications, Los Altos, Calif., Fourth Edition) and references cited therein, as well as in Harlow and Lane (1988).

As described above, the antibody of the present invention can bind an antigen which is attached to the nucleic acid probe. The antibody itself can be linked to a detectable moiety, such as an enzyme, and binding of antibody to an antigen attached to a nucleic acid probe can thereby be detected directly. Alternatively, the antibody which binds the antigen which is attached to the nucleic acid probe can be detected indirectly, by binding a second antibody which recognizes the first bound antibody as an antigen. The second antibody can be linked to a detectable moiety, such as an enzyme, thereby detecting the binding of the first antibody indirectly.

In the present invention, the spectral image of the biological sample on the substrate can be obtained with a device which utilizes a common path Sagnac interferometer creating an optical path difference based on the angle of incident light. An interferogram is produced showing the light intensities against the function of the optical path difference. Fourier transformation of the interferogram recovers the spectrum. An example of this device is a SD200 Spectracube (Applied Spectral Image, Migdal HaEmek, Israel). Other methods to measure absorption spectra using light microscopy can include spectrophotometry, the use of liquid crystal tunable filters and accusto-optical tunable filters.

The spectral image of the biological sample of this invention can be analyzed with software designed for spectral image analysis, such as the SpCube 1.5 program (Applied Spectral Imaging). The present invention further contemplates software programs dedicated to the methods of this invention.

The following examples are intended to illustrate, but not limit, the invention. While the protocols described are typical of those that might be used, other procedures known to those skilled in the art may be alternatively employed.

EXAMPLES

Biological Specimens

T24 human bladder cancer cells (ATCC accession number ATCC HTB 4) were grown on microscope slides under standard cell culture conditions to 30% confluency. Cells were fixed and pretreated for in situ hybridization as described (Speel et al., 1994). Human spermatozoid cells were obtained from a healthy male, fixed and smeared on a microscopic slide for pretreatment for in situ hybridization (Martini, E., et al., 1995. Application of different in situ hybridization detection methods for human sperm analysis." Hum. Reprod. 10:855–861).

T24 bladder cells were hybridized with centromeric alpha-satellite probes for chromosome 1, 7, 15 (Oncor, Gaithersburg, Md.) or combinations thereof. The sperm cells were hybridized with probes for X- and Y-chromosome specific loci (Oncor, Gaithersburg, Md.). For single labeling, probes were labeled by nick-translation with biotin (Boehringer-Mannheim, Germany) and detected with peroxidase (PO) conjugated to avidin (Vector, USA) or alkaline phosphatase (AP) conjugated to avidin (Vector), depending on the enzyme substrate to be used. Diaminobenzidine (DAB), tetra-methylbenzidine (TMB) and amino-ethyl-carbazole (AEC) were used as substrates for PO and New Fuchsin (NF), Fast Red (FR) and NBT/BCIP/INT (INT) were used as substrates for AP. (Substrates were obtained commercially.) The enzyme reaction produces a precipitate, i.e. a chromogenic dye, in situ that is visible in a bright field light microscope.

For double labeling, one probe was labeled with biotin and the other with digoxigenin (Boehringer-Mannheim). Digoxigenin label was detected with polyclonal anti-digoxigenin antibody conjugated to either PO or AP (Boehringer-Mannheim). The third label was introduced by using fluorescein isothiocyanate (FITC) as a hapten and detected with mouse anti-FITC antibody (Dako, Denmark) and anti-mouse-PO or anti-mouse-AP antibody (Boehringer). In double and triple labeling, interspecies cross-reactivity was blocked and enzyme reactions producing the reporter signals were developed sequentially (Speel et al., 1994).

Nuclei of T24 bladder cells were stained either lightly or heavily with hematoxylin and sperm cells were cytologically stained with DIFF QUIK. Simultaneous staining with cytochemical stains such as, for example, hematoxylin (blue/purple), methyl green, eosin (pink) or DIF Quick (red) provides histological information and contributes to multi-parameter bright-field microscopic analysis. Specimens were covered with mounting medium (obtained commercially) under a coverslip.

Microscopy

A Leica DM microscope was equipped with a SD200 SpectraCube (Applied Spectral Image, Migdal HaEmek, Israel) for acquisition of spectral images. A halogen transmission light operating at 12 V for daylight color temperature was used in the visible range (400–700 nm) by placing a WG360 UV cut-off filter and a BG38 infrared cut-off filter in the illumination pathway. Neutral density filters were used to optimize the light level for spectral imaging. Spectral images were acquired with ASI acquisition software running on a Dell Pentium PC. Typically, a spectral image is built of 200 frames of 300 ms with an interferometer stepsize angle of 15 degrees. Spectral analysis was performed on SpCube1.5 analysis software (ASI).

Spectral imaging using the SD200 SpectraCube mounted on a transmission light microscope allows for the measurement of the absorption spectra of chromogenic dyes while retaining the spatial information of the microscopic image. A spectral image is acquired and for every pixel in the CCD image the absorption spectrum can be retrieved. The so-called 'optical density image' displays the constituents of the specimen that absorb the light of certain wavelengths. Regions that do not absorb light appear black. For every pixel, an absorption curve can be produced, showing the absorption intensities per wavelength. Pixel by pixel spectral data can be utilized for subsequent mathematical operations. For example, a spectrum-based classification would result instantly in the pseudo-colorization of pixels with similar spectra. Defining spectral signatures for specific regions within a specimen provides flexibility for image analysis.

To demonstrate the improvement in clinical diagnosis provided by the methods of the present invention as compared to techniques available at the time the present invention was made, a comparison was made between the bright field spectral imaging technology of the present invention and state-of-the-art quantitative microscopy software. For the latter procedure, a 3-chip color charged couple device (CCD) video camera and Leica QWin software were used for image capture and quantitative hue, as well as saturation and intensity measurements. The hue value is a trivial but fixed number for every color, whereas the saturation and intensity values vary dependent on the quality of the detection. Color discrimination in a 3-color video image therefore should be based on hue values. Hue values are displayed in a histogram, showing the number of pixels in an image for every hue value. Pixels with hue values which match exactly can be selected and displayed with a single pseudo-color. Hue-classification of all pixels in the image simultaneously is not possible in a single operation.

For comparison of the spectral imaging method of the present invention with quantitative microscopy, the same microscope was equipped with a 3-chip color charged couple device camera (Sony, Japan) controlled by QWin software (Leica Imaging, Cambridge UK), for image acquisition and quantitative analysis, operating on a Leica Q550 Pentium PC. Video images were acquired with a halogen transmission light at 12 V (or 10.5V with a CB12 blue filter to correct for daylight color temperature) and neutral density filters for optimal video exposure times.

Figure 1:
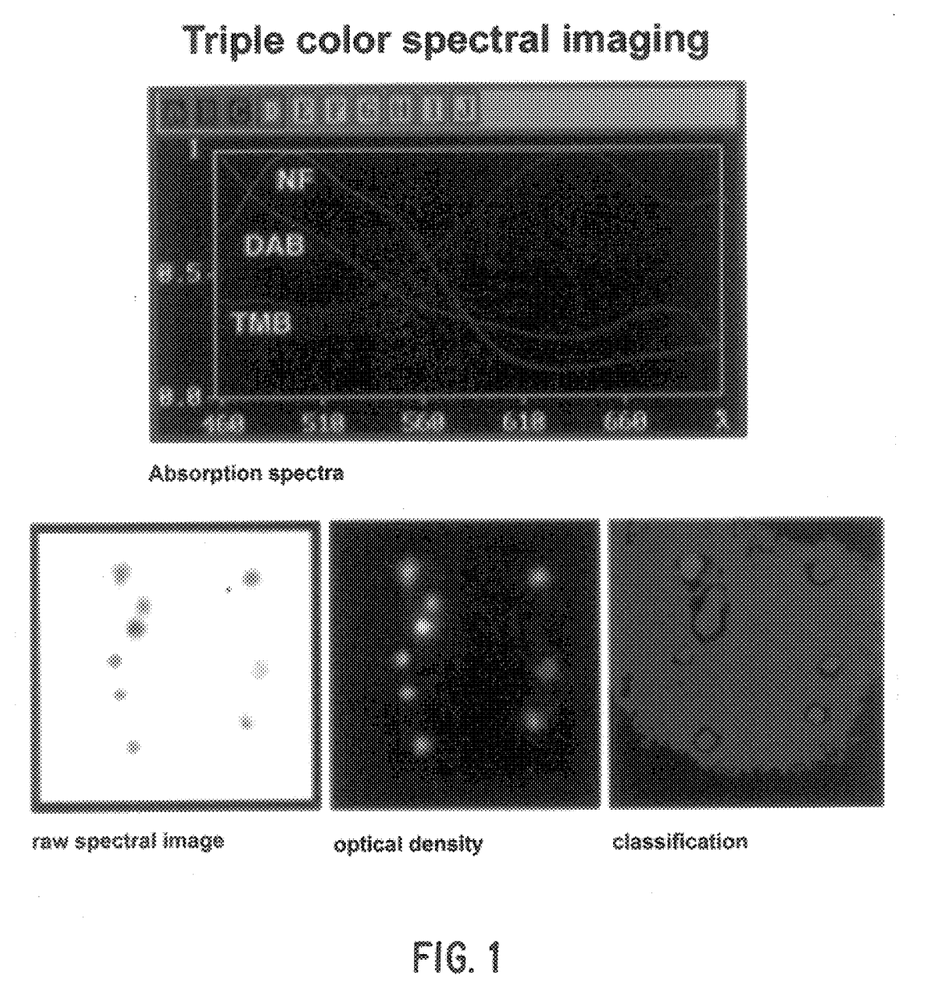

The in situ hybridization signals (spots) for centromere sequences in T24 bladder cancer cells were analyzed after single-color labeling, double-color labeling and triple-color labeling, with and without cytological counterstaining. Single labeling experiments without counterstain showed the spectra of the pure dyes. The absorption spectra of the PO substrates DAB, TMB, and AEC and of the AP substrates Fast Red, New Fuchsin and INT were measured, showing specific spectral characteristics for each dye. Spectral imaging of a triple-color in situ hybridization for chromosome centromeres using TMB (green), New Fuchsin (red) and DAB (brown) as reporter dyes resulted in good spectral separation of the individual dyes (FIG. 1). Even the colors of small spots that could not be easily discerned by eye were readily identified. The absorption peaks were wide apart and the shapes of the curves deviated clearly to allow for a spectrum-based color classification of all spots.

In comparison, video images were acquired using a 3-chip color CCD camera. Based on color hue values, the presence of the three colors could be discriminated in a histogram. Hue measurement results, however, could not be shown within the cellular context after a single operation.

Figure 2:
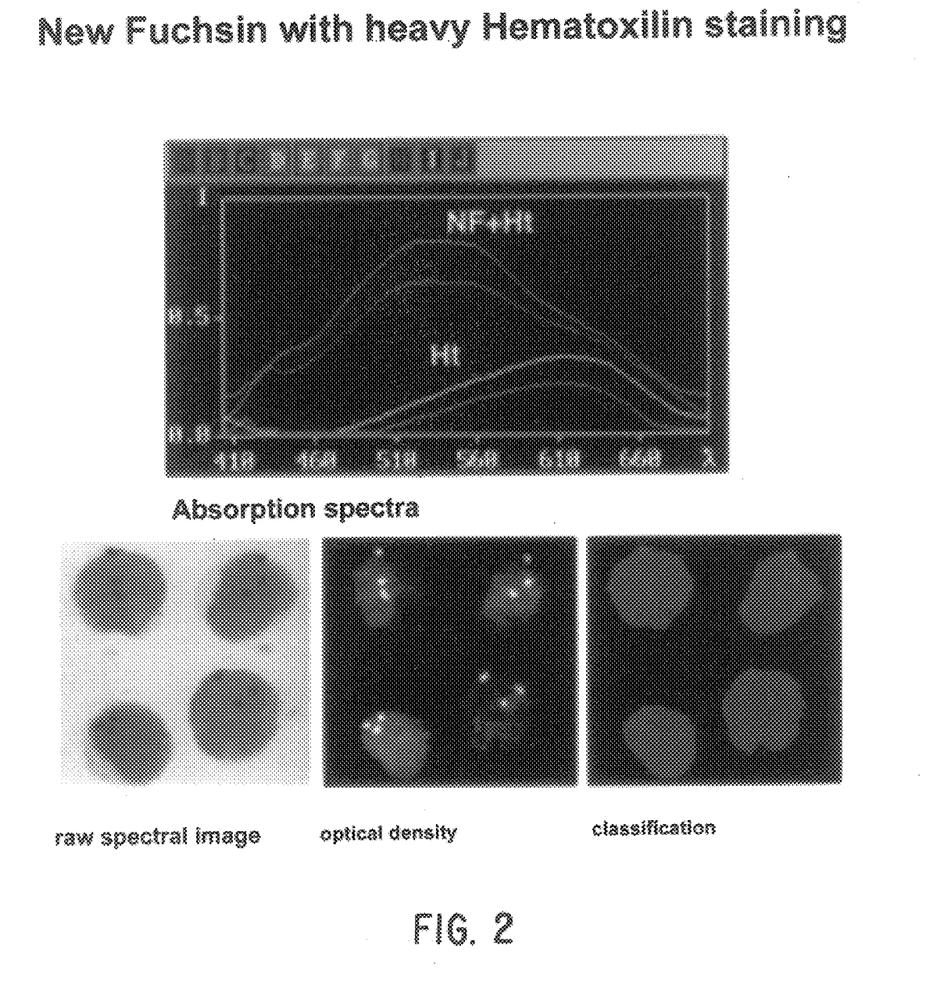

When cytological stains such as hematoxylin (blue purple) and DIF Quick (red) are used, they are present throughout the cell or cell compartment and are thus overlaying the hybridization spots. The absorption spectrum of two co-localizing dyes seems to be additive, meaning that the spectrum of the overlap is the sum of the two pure spectra. The spectrum that is measured at the hybridization spots is, therefore, mixed with the spectrum of the cytological stain. The use of cytological stains, however, did not compromise the separation of the absorption spectra of the reporter dyes (FIG. 2). In single labeling experiments using New Fuchsin and heavy nuclear staining with hematoxylin, the absorption spectrum of New Fuchsin had shifted but this did not create a problem for the classification of the hybridization signals.

Figure 3:
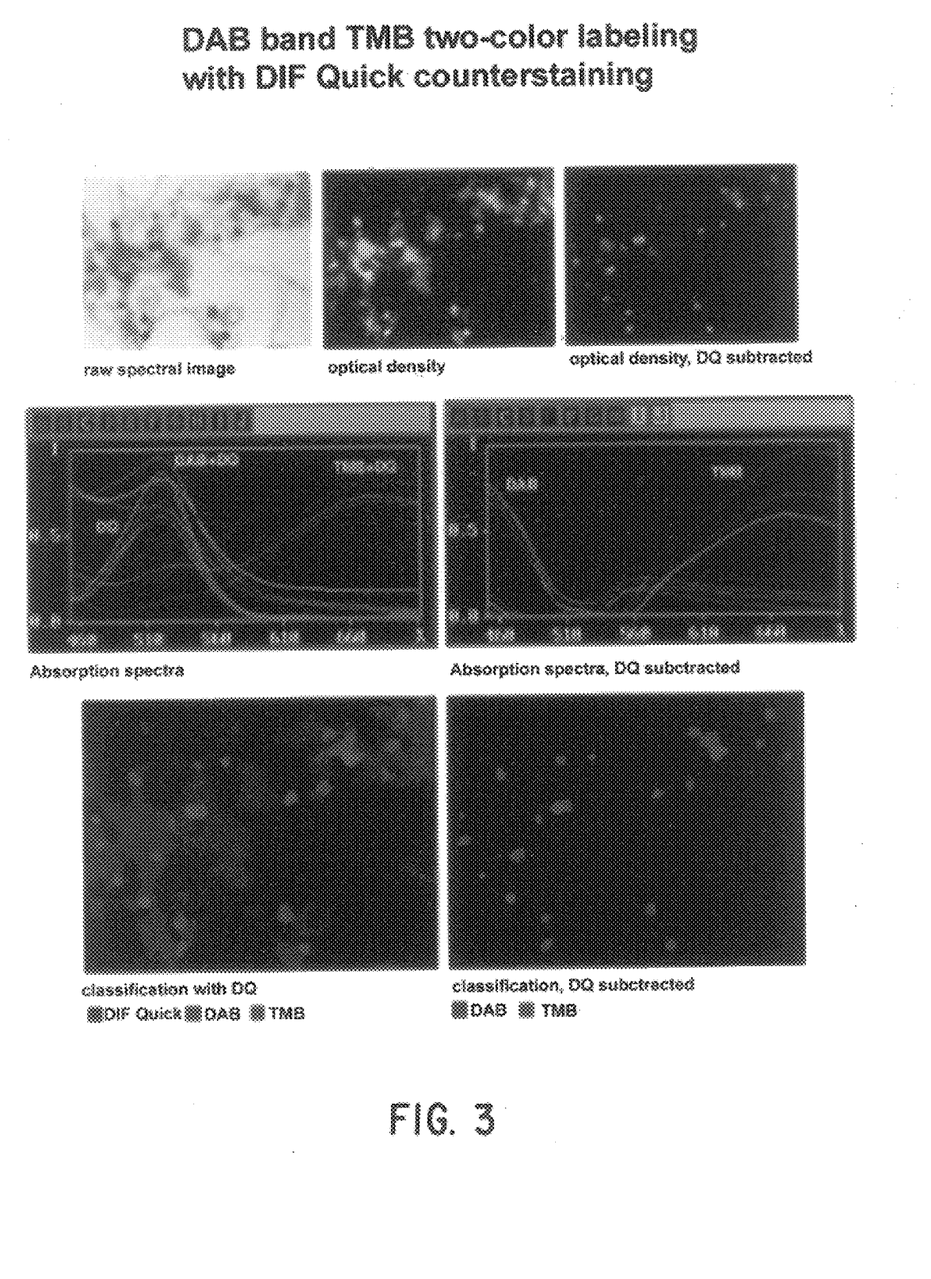
FIG. 3. Double target in situ hybridization on sperm cells of a healthy human, using a chromosome X centromere probe visualized with DAB and a chromosome Y centromere probe visualized with TMB, combined with histomorphologic staining with DIFF QUIK, a commercially available eosin derivative stain. The sperm cells contain a signal either for the X chromosome or the Y chromosome. Top left shows the raw spectral image in arbitrary display colors. It was difficult to determine the color by eye through the microscope, due to weak spots and overall cytoplasmic staining and overlapping regions as a result of the preparation (smear) technique. Top center shows the spectral image after calculation of the absorption spectra displayed in complementary colors. Middle left shows the spectra of selected pixels for DAB, TMB spots and DIFF QUIK. The spectra of the spots are mixed with the spectrum of DIFF QUIK. Bottom left shows the classification based on the average spectrum of these pixels, false-coloring DAB spots in brown, TMB spots in green and DIFF QUIK staining above a certain intensity threshold in blue. A more accurate classification was achieved when the spectrum of the morphological staining was eliminated from the spectral image by subtraction or division. Top right shows the subtracted image. Bottom right shows the classification based on the average spectrum of these pixels, displaying just the hybridization spots in false colors brown (DAB) and green (TMB).

In a double labeling experiment on sperm cells, using X and Y chromosome-specific probes reported with, respectively, DAB and TMB, and cytologically stained with DIF Quick, clear spectral signatures of all three dyes can be defined (FIG. 3). Spectrum based classification including all three dyes showed the hybridization spots of X and Y in pseudo-colors which would have been difficult from microscopic evaluation alone. The SpCube analysis software provides for mathematical operations such as spectrum subtraction and division. By selecting the average spectrum of DIF Quick, a subtraction operation was executed, eliminating the contribution of the cytological stain from the spectral image. A similar effect can be achieved by division. The classification image of FIG. 3 shows just the hybridization spots.

In contrast, with the quantitative microscopy software, hue measurements of single and double labeling experiments with counterstaining were not consistently successful. Due to lower color resolution, dyes of similar hue could not be discriminated in the hue-histogram. Under influence of cytological stains, the hue values of the hybridization spots shifted towards the hue of the stain, which led to 'drowning' of the spot in cases of intense cytological staining or low hybridization signals. This phenomenon could not be prevented because mathematical subtraction/division operations can not be executed on these video images.

These data demonstrate that the bright field spectral imaging method of the present invention provides for analysis of absorption spectra with high precision while maintaining spatial information. The use of cytological stains doesn't hamper spectral analysis and thus greatly facilitates microscopic evaluation.

With quantitative microscopy, color discrimination based on hue value using QWin software is possible by manually selecting spots. However, cytological staining readily obscures color discrimination. Using QWin software, the hue measurement results can not be displayed together with spatial information in a single operation. Thus, the data presented herein demonstrate that the spectral imaging methods of the present invention provide higher color resolution than 3-color video imaging, enabling the color discrimination necessary for reliable and user-friendly multi-parameter analysis of multi-color specimens.

Detection of Phenotypic and Genetic Markers
According to the Method of the Present Invention
for Detection, Diagnosis, Characterization and
Prognosis of Cervical Cancer.

The diagnosis and staging of cancer is often not possible without combining the results from several analyses. This includes: 1) the interpretation of histomorphology after applying routine stains; 2) the complementation of those histomorphological analyses with pertinent genetic markers, such as the gain of 3q in cervical cancers as definite identifiers of tumor progression; and 3) the necessity to include phenotypic analysis by means of immunohistochemistry with antibodies against commonly deregulated oncogenes and tumor suppressor genes such as p53 and/or the presence on viral genes such as human papilloma virus (HPV). Multi-parameter analysis would benefit from the simultaneous assessment of the above mentioned markers, which is possible, but very difficult using fluorescence. Bright field with permanent dyes comes with the described advantages, however, color discrimination is a challenge. Spectral imaging overcomes these limitations by allowing detection of multiple targets in pathological specimens simultaneously.

As a specific example, in the progression of cervical carcinoma in situ into invasive cervical carcinoma, an amplification of chromosome region 3q24-28 is observed by comparative genomic hybridization (CGH). This is the only detectable genetic event at this stage of carcinogenesis and is therefore suitable as a diagnostic marker for early-stage cervical carcinoma. CGH analyses of late-stage cervical carcinomas revealed chromosomal gains in regions of 2q and 5p. Cervical specimens can be biopsies, smears, cytospin preparations, or sections of embedded cells. Comprehensive diagnosis includes assessment of: 1) cytomorphology, using morphological stains such as hematoxylin and eosin; 2) detection of HPV genome by in situ hybridization; 3) screening for genotypic markers 3q, 2p and 5p; 4) screening for tumor suppressor gene products p53 and Rb, both known to interact with HPV antigens; and 5) screening for other phenotypic markers such as Ki67 and other markers associated with the aggressiveness of tumors.

Although the present process has been described with reference to specific details of certain embodiments thereof, it is not intended that such details should be regarded as limitations upon the scope of the invention except as and to the extent that they are included in the accompanying claims.

Throughout this application, various publications are referenced. The disclosures of these publications in their entireties are hereby incorporated by reference into this application in order to more fully describe the state of the art to which this invention pertains.

What is claimed is:

1. A method for detecting a genetic marker in a biological sample comprising:

a) contacting the biological sample with a nucleic acid probe linked to a detectable moiety, whereby the detectable moiety can be detected by the presence of a chromogenic dye associated with the detectable moiety;

b) obtaining a spectral image of the biological sample using brightfield microscopy; and c) detecting the presence of the chromogenic dye, thereby detecting the genetic marker in the biological sample.

2. The method of claim 1, wherein the biological sample is contacted with nucleic acid probes having at least two different specificities.

3. The method of claim 1, wherein the biological sample is attached to a substrate.

4. The method of claim 1, wherein step (a) further comprises contacting the biological sample with a cytological stain.

5. The method of claim 1, wherein step (c) further comprises distinguishing the cytological stain from the detectable moiety.

6. The method of claim 1, wherein the genetic marker is selected from the group consisting of a centromere, a telomere, a general genetic loci, a specific genetic loci, a chromosome band, a chromosome-specific loci, a chromosome fragment, and a whole chromosome.

7. The method of claim 1, wherein the detectable moiety comprises a hapten.

* * * * *